US00PP12186P2

(12) United States Plant Patent
Gilford et al.

(10) Patent No.: US PP12,186 P2
(45) Date of Patent: Nov. 6, 2001

(54) STRAWBERRY PLANT NAMED 'BISCAYNE'

(75) Inventors: Kristie L. Gilford, Dover, FL (US); Bruce D. Mowrey, Watsonville, CA (US); Jorge Campos Garcia, Plant City, FL (US); Thomas M. Sjulin, Aromas; Larry T. Kodama, Freedom, both of CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 09/396,214

(22) Filed: Sep. 15, 1999

(51) Int. Cl.[7] ..... A01H 5/00
(52) U.S. Cl. ..... Plt./209
(58) Field of Search ..... Plt./208, 209

(56) References Cited

U.S. PATENT DOCUMENTS

P.P. 8,649 3/1994 Sjulin et al. ..... Plt./208

OTHER PUBLICATIONS

U.S. application No. 08/858,843, Mar. 7, 2000, Strawberry plant named 'Captiva', filed May 19, 1997.
U.S. application No. 08/862,821, Mar. 7, 2000, Strawberry plant named 'Mirador', filed May, 23, 1997.

*Primary Examiner*—Bruce R. Campell
*Assistant Examiner*—Michelle Kizilkaya
(74) *Attorney, Agent, or Firm*—Pennie & Edmonds LLP

(57) ABSTRACT

This invention relates to a new and distinct variety of strawberry named 'Biscayne', botanically identified as *Fragaria×ananassa*. The closest known varieties are 'Key Largo' (U.S. Plant Pat. No. 8,649), 'Captiva' (U.S. Plant Pat. No. 11,277, allowed) and 'Mirador' (U.S. Plant Pat. No. 11,279, allowed). The new variety is a partially everbearing fruit bearing variety. The variety is distinguished from 'Key Largo' by its strong plant vigor, concave cross section of the leaf, rounded teeth on the terminal leaflet, outward pose of the petiole hairs, larger to the same size diameter of the calyx relative to the corolla, medium fruit glossiness, strong adherence of the calyx to the fruit, fruit of soft to medium firmness, medium to early time of flowering and early harvest maturity.

2 Drawing Sheets

1. BACKGROUND OF THE INVENTION

The new variety originated as a result of a controlled cross between the strawberry plants 'Key Largo' (U.S. Plant Pat. No. 8,649) and 'L3' (unpatented proprietary) in an ongoing breeding program, and was discovered as a seedling in a controlled breeding plot. The original seedling of the new cultivar was asexually propagated by stolons in Shasta County, California. Propagules were transplanted to a controlled breeding plot in Valrico, Hillsborough County, Fla. where the new cultivar first fruited in December 1994 and was selected for further evaluation. 'Biscayne' was subsequently asexually propagated and underwent further testing in the area of Valrico, Fla. from 1995–1999. This propagation and testing has demonstrated that the combination of traits disclosed herein which characterize the new variety are fixed and retained true to type through successive generations of asexual reproduction.

2. SUMMARY OF THE INVENTION

The present invention relates to a new and distinct variety of strawberry named 'Biscayne'. The variety is botanically identified as *Fragaria×ananassa*. The new variety is distinguished from other varieties by a number of characteristics as set forth in Tables 1, 2 and 3.

3. COMPARISON TO CLOSEST VARIETIES

The vartieties which we believe to be closest to 'Biscayne' from those known to us are 'Key Largo' (U.S. Plant Pat. No. 8,649), 'Captiva' (U.S. Plant patent application Ser. No. 08/858,843, allowed) and 'Mirador' (U.S. Plant patent application Ser. No. 08/862,821, allowed). There are several characteristics of 'Biscayne' that are different from, or not possessed by 'Key Largo', 'Captiva' or 'Mirador'. Table 1 provides information on the plant and fruit characteristics of the new variety 'Biscayne' compared with characteristics of 'Key Largo', 'Captiva' and 'Mirador'. Table 2 provides additional information of the plant and fruit characteristics of the new variety 'Biscayne' compared with characteristics of the varieties 'Captiva', 'Key Largo', and 'Mirador'. Table 3 provides isozyme characteristics of the new variety as compared to the varieties 'Key Largo', 'Captiva' and 'Mirador'.

4. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

5. DESCRIPTION OF THE NEW VARIETY

Figure 1:
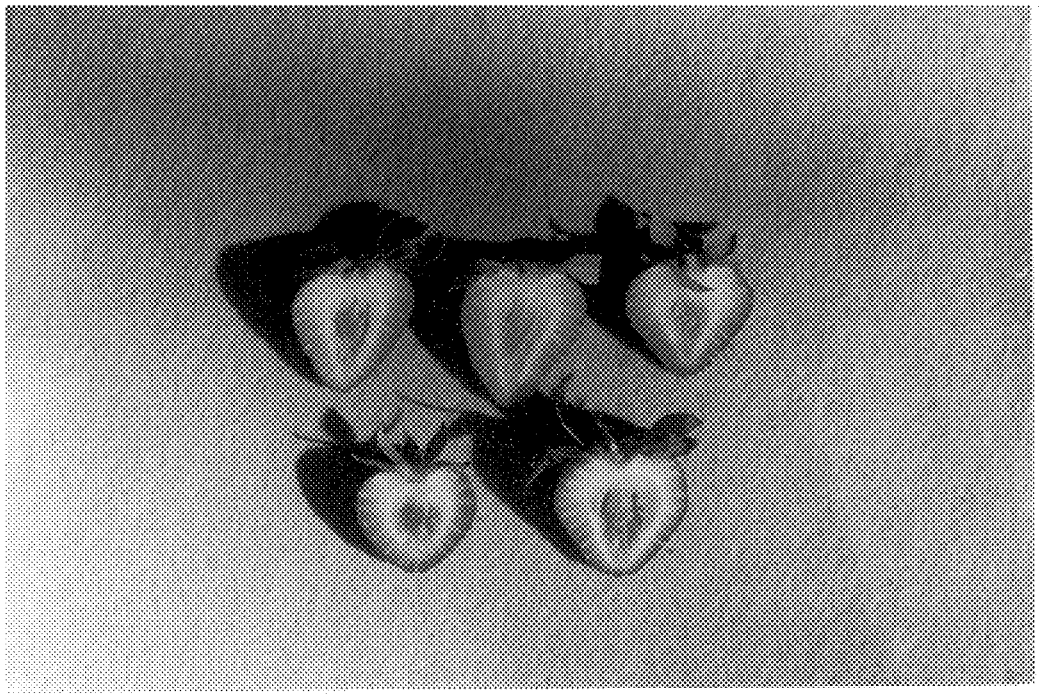
FIG. 1 shows the fruit in longitudinal section, illustrating the typical flesh coloration.
Figure 2:
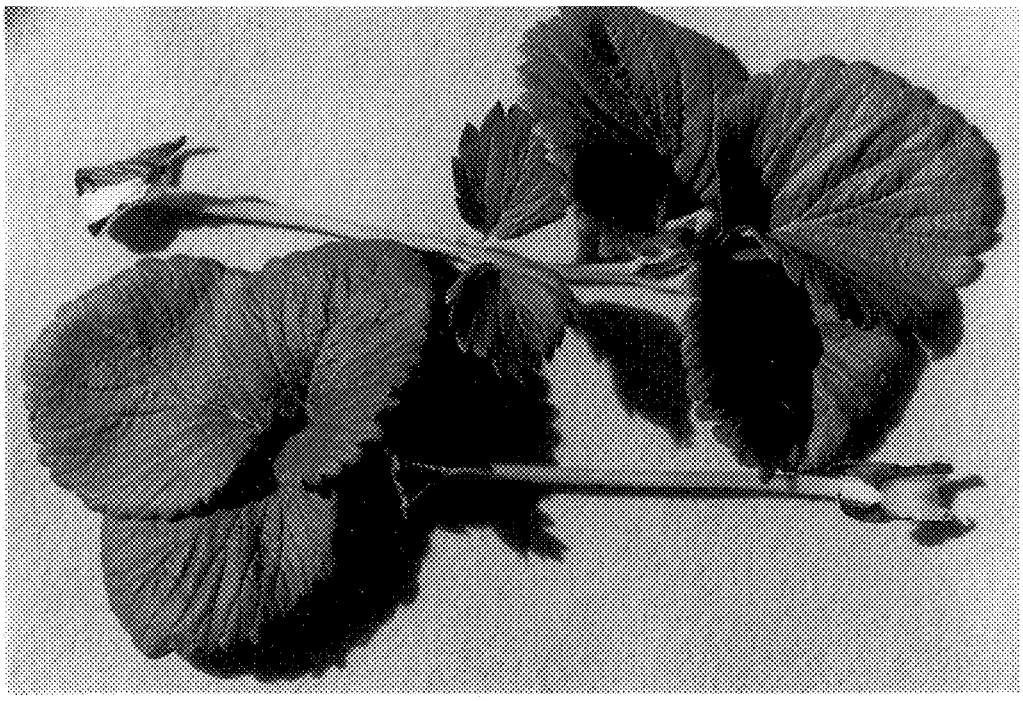
FIG. 2 shows the upper surface of the two typical folioles of the new variety.
Figure 3:
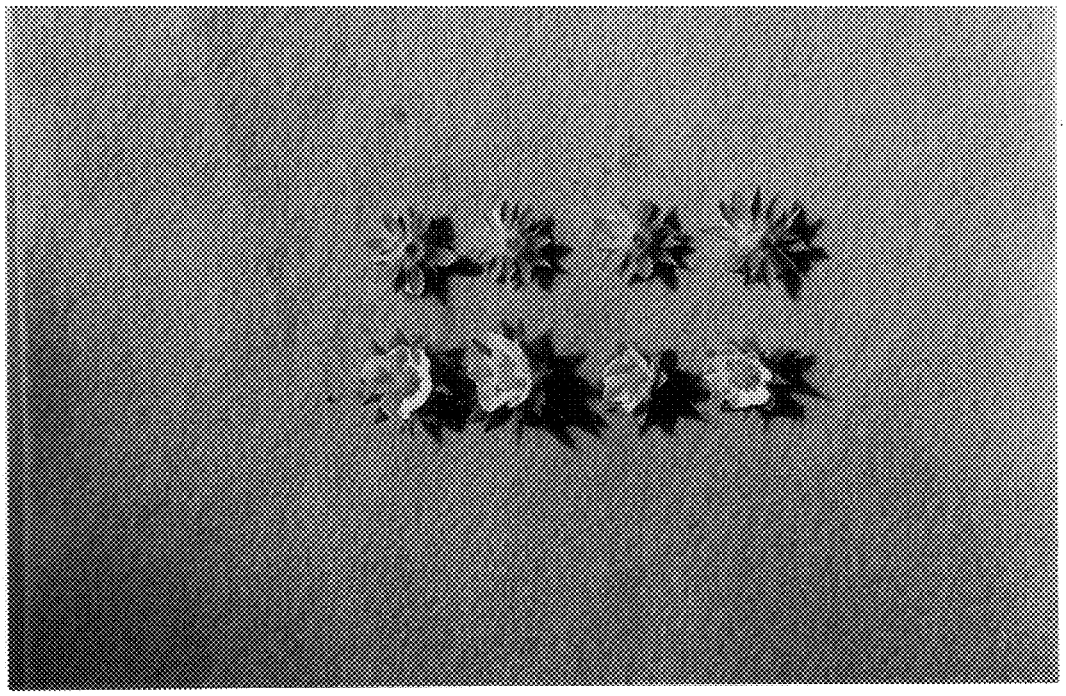
FIG. 3 shows the flower and reproductive organs of the new variety, as well as the size and position of the petals and sepals and the underside of the calyx.
Figure 4:
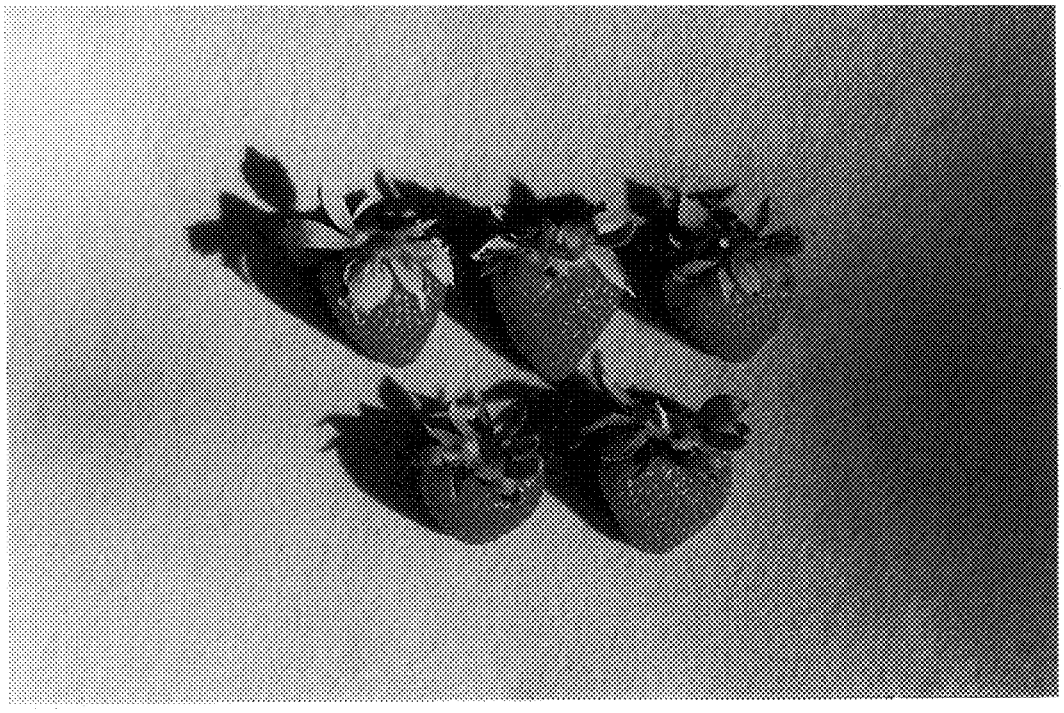
FIG. 4 shows typical whole fruit.

This following detailed description of the new variety is based upon observations taken of plants and fruit grown in Valrico, Fla., U.S.A. Observations of 'Biscayne', 'Key Largo', 'Captiva' and 'Mirador' were taken in side by side comparison in 1999. This description is in accordance with UPOV terminology. Color designations, color descriptions, and other phenotypical descriptions may deviate from the stated values and descriptions depending upon variation in environmental, seasonal, climatic and cultural conditions. Colors are described and the closest matching color ratings are provided using The Royal Horticultural Society (R.H.S.) Colour Chart.

5.1 Propagation

The new variety is principally propagated by way of stolons. Although propagation by stolons is presently preferred, other known methods of propagating strawberry plants may be employed.

5.2 Characteristics of the New Variety

Information on the new variety is presented in Tables 1, 2 and 3. In the tables, the flowers described are secondary flowers except where indicated. Petal color of 'Biscayne' is white which is not referenced in The Royal Horticultural Society Colour Chart. The fruit described is the secondary fruit on one year old plants. Fruit and flower measurements are an average of both primary and secondary fruit and flowers, respectively.

PLANTS AND FOLIAGE

Plants of 'Biscayne' are of strong vigor compared to medium vigor for 'Captiva', 'Key Largo' and 'Mirador'. The habit of 'Biscayne' is flat globuse while that of 'Key Largo' and 'Mirador' is globuse. The density of 'Biscayne' is medium compared to open for 'Mirador'. The average plant height is 20.4 cm, the average plant diameter is 39.5 cm, and the average number of crowns/plant is 3.3.

The upperside of 'Biscayne' leaves are dark green with an RHS color rating of 137A. The underside of the leaves is light green having an RHS color rating of 139C.

The leaf profile is concave and there is weak interveinal leaf-blistering. The plants have three leaflets only. The terminal leaflet margin profile is revolute and the length-to-width ratio of the terminal leaflet is broader than long. The leaves have medium glossiness. The shape of the base of the terminal leaflet is rounded and the average number of teeth per terminal leaflet is 28.5. The average length and width of the terminal leaflet are 9.2 cm and 9.8 cm, respectively.

The petiole has dense pubescence and the pose of the petiole hairs is outwards. The average petiole length is 12.7 cm. The petiole color has an RHS color rating of 144B.

The bract frequency is 100% and the bracts typically occur in pairs compared to 'Captiva' and 'Mirador' having single bracts occurring with a frequency of 60%.

The stipule length and width are 4.2 cm and 2.3 cm, respectively. The stipule pubescence is sparse.

'Biscayne' has numerous stolons that are of medium thickness with strong anthocyanin coloration and medium pubescence.

FLOWER AND FRUIT CHARACTERISTICS

The position of the 'Biscayne' inflorescence is level with the foliage compared to that of 'Key Largo', 'Captiva' which are beneath and 'Mirador' which is above. The flowers are medium in size. The average petal length and width are 1.3 cm and 1.5 cm, respectively. The average flower diameter is 3.4 cm. The average calyx diameter is 4.4 cm.

The diameter of calyx is larger than the corolla. On secondary flowers, the diameter of the inner calyx is the same size as the outer calyx. On secondary flowers with 5 to 6 petals, the petals are overlapping. The petal length-to-width ratio on secondary flowers is broader than they are long compared to 'Key Largo', and 'Captiva' which are as long as broad.

The fruiting trusses are long in length with an average length of 17.1 cm from the crown to the base of the terminal flower or fruit. The attitude at first picking is semi-erect compared with prostrate and erect for 'Captiva' and 'Mirador', respectively.

Observations of 'Biscayne' fruit were taken of secondary fruit on one year old plants. The fruit are predominantly conical in shape. The fruit length to maximum width ratio is longer than broad. The fruit are medium in size. The average length and width of the fruit are 3.8 cm and 3.7 cm, respectively. There is a slight differencce in fruit shape between the primary and secondary fruits. The band without achenes is narrow. The fruit surface has a weak unevenness.

The fruit skin color is even and red with an RHS color rating of 46B and has medium glossiness.

The insertion of the achenes is level with the surface of the fruit.

The calyx is inserted with the fruit and the pose of the calyx segments is spreading compared to that of 'Key Largo' which is reflexed. The calyx diameter is larger than the fruit diameter. The adherence of the calyx to the fruit is strong.

The fruit flesh is firm when fully ripe. The color of the fruit flesh is medium red with an RHS color rating of 44A. The fruit flesh color is slightly uneven, and the fruit flesh color distribution is marginal and central. The fruit has a large sized hollow center.

The fruit has a medium sweetness, with medium acidity and fine texture.

The time of flowering when 50% of the plants are at first flower early, Initial flowering occurs in late-October to early-November.

The harvest maturity when 50% of the plants possess ripe fruit is early. Season of harvest is from late-November through early-April. 'Biscayne' is partially everbearing variety.

The average number of stamens is 29.

Anthocyanin coloration is red to purple red.

The average number of pedicels/peduncle is 4.2. Average peduncle diameter is 4.5 mm and average peduncle length is 13.9 cm. The average pedicel diameter is 2.2 mm and average pedicel length is 9.5 cm. Average petiole diameter is 3.4 mm.

Achene insertion is level with surface. Achene color is yellow to red (13B to 46A).

The average number of sepals is 10.5. Average sepal length 1.14 cm.

Percent brix is 9.4. The amount of pollen produced is abundant and fertile.

TABLE 1

DETAILED COMPARISON OF 'BISCAYNE', 'KEY LARGO', 'CAPTIVA' AND 'MIRADOR'

| | BISCAYNE | KEY LARGO | CAPTIVA | MIRADOR |
|---|---|---|---|---|
| Plant Characteristics | | | | |
| Height of Plant | 20.4 cm | 18.3 cm | 13.0 cm | 20.0 cm |
| Spread of Plant | 39.5 cm | 39.2 cm | 33.1 cm | 35.0 cm |
| Number of Crowns | 3.3 cm | 4.0 cm | 4.4 cm | 3.0 cm |
| Leaf Characteristics | | | | |
| Terminal Leaflet Width | 9.8 cm | 8.9 cm | 7.3 cm | 9.0 cm |
| Terminal Leaflet Length | 9.2 cm | 8.5 cm | 7.2 cm | 8.3 cm |
| Terminal Leaflet Length/Width Ratio | 0.94 | 0.96 | 0.99 | 0.92 |
| Number of Teeth/ Terminal Leaflet | 28.5 | 23.8 | 25.4 | 20.0 |
| Petiole Length | 12.7 cm | 10.4 cm | 8.1 cm | 12.8 cm |
| Bract Frequency | 100% Typically in pairs | 30% Typically in pairs | 60% Typically single | 60% Typically single |
| Stipule Length | 4.2 cm | 3.7cm | 3.6 cm | 3.6 cm |
| Stipule Width | 2.3 cm | 1.9 cm | 1.8 cm | 2.2 cm |
| Flower Characteristics | | | | |
| Petal Width | 1.5 cm | 1.5 cm | 1.4 cm | 1.6 cm |
| Petal Length | 1.3 cm | 1.5 cm | 1.4 cm | 1.5 cm |
| Petal Length/ Width Ratio | 0.87 | 1.00 | 1.00 | 0.94 |
| Flower Diameter | 3.4 cm | 3.9 cm | 3.6 cm | 4.0 cm |
| Calyx Diameter | 4.4 cm | 5.1 cm | 4.3 cm | 4.0 cm |
| Fruit Characteristics | | | | |
| Fruit Width | 3.7 cm | 3.5 cm | 3.6 cm | 3.5 cm |
| Fruit Length | 3.8 cm | 4.2 cm | 4.1 cm | 3.5 cm |
| Fruit Length/ Width Ratio | 1.03 | 1.20 | 1.14 | 1.00 |
| Average Berry | Medium | Medium | Medium | Small |
| Weight (g) | 19.8 g | 22.4 g | 17.8 g | 16.3 g |
| Fruit Skin | Red | Dark Red | Light Red | Pale Rose |
| Color | 46B | 46B | 45A | 45B |
| Fruit Flesh | Medium Red | Light Red | Light Red | Pale Rose |
| Color | 44A | 44C | 49C | 43B |
| Total Yield (g/plant) | 430 | 277 | 369 | 551 |

TABLE 2

CHARACTERISTICS OF 'BISCAYNE', 'KEY LARGO', 'CAPTIVA' AND 'MIRADOR'

| | BISCAYNE | CAPTIVA | KEY LARGO | MIRADOR |
|---|---|---|---|---|
| Plant | | | | |
| Habit | Flat globuse | Flat globuse | Globuse | Globuse |
| Density | Medium | Medium | Medium | Open |
| Vigor | Strong | Medium | Medium | Medium |
| Leaf | | | | |
| Color of upper side | Dark green 137A | Dark green 137A | Dark green 137A | Dark green 137A |
| Color of under side | Light green 139C | Light green 139C | Light green 139C | Light green 139C |
| Shape in cross section | Concave | Slightly Concave | Slightly Concave | Slightly Concave |
| Interveinal | Weak | Weak | Weak | Weak |

TABLE 2-continued

CHARACTERISTICS OF 'BISCAYNE', 'KEY LARGO', 'CAPTIVA' AND 'MIRADOR'

| | BISCAYNE | CAPTIVA | KEY LARGO | MIRADOR |
|---|---|---|---|---|
| blistering | | | | |
| Glossiness | Medium | Medium | Medium | Medium |
| Number of leaflets | 3 | 3 | 3 | 3 |
| Terminal leaflet margin profile | Revolute | Revolute | Revolute | Revolute |
| Terminal leaflet shape of base | Rounded | Obtuse | Slightly oblique | Slightly oblique |
| Terminal leaflet shape of teeth | Rounded | Obtuse | Rounded | Rounded |
| Terminal leaflet average number of teeth | 28.5 | 25.4 | 23.8 | 20.0 |
| Petiole pubescence | Dense | Medium | Medium | Medium |
| Petiole pose of hairs | Outwards | Upwards | Upwards | Outwards |
| Petiole color | 144B | 141C | 141C | 141C |
| Stipule: pubecence | Sparse | Medium | Medium | Sparse |
| Bracts frequency on petioles | 100%. Typically in Pairs | 60%; Typically single | 30%, Typically in pairs | 60% Typically single |
| Stolon | | | | |
| Number | Many | Medium to many | — | Many |
| Anthocyanin coloration | Strong | Strong | — | Medium to strong |
| Thickness | Medium | Medium to thick | — | Thin to Medium |
| Pubescence | Medium | Sparse to Medium | — | Sparse to Medium |
| Inflorescence | | | | |
| Position relative to foliage | Level | Beneath | Beneath | Above |
| Flower size | Medium | Medium | Large | Small |
| Diameter of calyx relative to corolla | Larger | Larger | Much larger | Same size |
| Diameter of inner calyx relative to outer | Same size | Smaller | Smaller | Smaller |
| Spacing of petals | Over-lapping | Over-lapping | Over-lapping | Over lapping |
| Fruiting Truss | | | | |
| Attitude at first picking | Semi-erect | Prostrate | Semi-erect | Erect |
| Length | 17.1 cm | 9.4 cm | 16.6 cm | 17.3 cm |
| Fruit | | | | |
| Weight (g) | 19.8 | 17.8 | 22.4 | 16.3 |
| Predominant shape | Conical | Conical | Conical | Conical |
| Difference in shapes between primary-and secondary fruits | Slight | Slight | Slight | Slight |
| Band without achenes | Narrow | Narrow | Narrow | Narrow |
| Unevenness of surface | Weak | Weak | Weak | Weak |
| Skin color | Red 46B | Orange Red 45A | Dark Red 46B | Red 45B |

TABLE 2-continued

CHARACTERISTICS OF 'BISCAYNE', 'KEY LARGO', 'CAPTIVA' AND 'MIRADOR'

| | BISCAYNE | CAPTIVA | KEY LARGO | MIRADOR |
|---|---|---|---|---|
| Evenness of color uneven | Even | Slightly even | Even | slightly even |
| Glossiness | Medium | Medium | Strong | Medium |
| Insertion of achenes | Level with surface | Level with surface | Below surface | Level with surface |
| Insertion of calyx | Level | Above fruit | Above fruit | Above fruit |
| Pose of the calyx segments | Spreading | Spreading | Reflexed | Spreading |
| Size of calyx in relation to fruit | Larger | Larger | Larger | Larger |
| Adherence of Calyx | Strong | Medium | Strong | Medium |
| Firmness of flesh | Firm | Firm | Firm | Firm |
| Color of flesh | Medium Red 44A | Light Red 49C | Light Red 44B | Pale Rose 43B |
| Evenness of flesh color | Slightly uneven | Slightly uneven | Slightly uneven | Slightly uneven |
| Distribution of flesh color | Marginal and central | Marginal and central | Marginal and central | Only marginal |
| Hollow center size | Large | Small | Medium | Medium |
| Sweetness | Medium | Medium | Medium | Medium |
| Texture when tasted | Fine | Fine | Medium | Fine |
| Acidity | Medium | Medium | Medium | Medium |

5.3 Insect and Disease Resistance and Susceptibility

The 'Biscayne' variety is moderately susceptible to *Xanthomonas fragariae* and Botrytis fruit rot. The variety is susceptible to Powdery Mildew and Verticillium wilt. The 'Biscayne' variety is also susceptible to injury by the two-spotted spider mite (*Tetranychus urticae*), lygus bug (*Lygus hesperus*) and Aphis spp (Aphids). 'Biscayne' is moderately resistant to Strawberry Mottle Virus.

5.4 Isozyme Analysis

In addition to the morphological description above, the new cultivar 'Biscayne' has been analyzed to obtain an indication of its genetic makeup to provide further means for identifying the new variety and distinguishing it from some other somewhat similar and/or related strawberry varieties. Specifically, leaf samples of 'Biscayne', 'Captiva', 'Key Largo' and 'Mirador' were analyzed by electrophoresis for isozyme patterns of the enzymes phosphoglucoisomerase (PGI), leucine aminopeptidase (LAP) and phosphoglucomutase (PGM). See *J. Amer. Soc. Hort. Sci.* 106:684–687. Isozyme characterization of the four varieties is presented in Table 3, with the letters representing the banding patterns for each enzyme as designated in the above-identified article.

TABLE 3

ISOZYME ANALYSIS FOR 'BISCAYNE' AND 'KEY LARGO', 'CAPTIVA' AND 'MIRADOR'

| Locus | BISCAYNE | CAPTIVA | KEY LARGO | MIRADOR |
|---|---|---|---|---|
| PGI | A1 | A2 | A1 | A3 |
| PGM | B3 | C2 | C4 | C4 |
| LAP | C4 | B3 | B3 | B3* |

*With slower migrating band staining more weakly than typical B3 pattern.

What is claimed is:

1. A new and distinct variety of strawberry plant, substantially as shown and described.

* * * * *